United States Patent [19]
Carati et al.

[11] Patent Number: 5,942,613
[45] Date of Patent: *Aug. 24, 1999

[54] PROCESS FOR THE PREPARATION OF AMIDES FROM OXIMES

[75] Inventors: Angela Carati; Carlo Perego; Leonardo Dalloro, all of Milan; Giordano De Alberti, Varese; Stefano Palmery, Milan, all of Italy

[73] Assignee: Enichem S.p.A., Milan, Italy

[*] Notice: This patent is subject to a terminal disclaimer.

[21] Appl. No.: 08/890,677

[22] Filed: Jul. 9, 1997

[30] Foreign Application Priority Data

Aug. 7, 1996 [IT] Italy ................. MI96A1716

[51] Int. Cl.$^6$ ................. C07D 201/04
[52] U.S. Cl. ................. 540/536
[58] Field of Search ................. 540/536

[56] References Cited

U.S. PATENT DOCUMENTS

| | | | |
|---|---|---|---|
| 4,281,194 | 7/1981 | Armor et al. | 564/267 |
| 4,359,421 | 11/1982 | Bell et al. | 260/239.3 |
| 4,709,024 | 11/1987 | Sato et al. | 540/536 |
| 4,745,221 | 5/1988 | Roffia et al. | 564/267 |
| 5,041,652 | 8/1991 | Padovan et al. | 564/267 |
| 5,334,368 | 8/1994 | Beck et al. | 423/704 |
| 5,625,108 | 4/1997 | Perego et al. | 585/520 |

*Primary Examiner*—Mukund J. Shah
*Assistant Examiner*—Bruck Kifle
*Attorney, Agent, or Firm*—Oblon, Spivak, McClelland, Maier & Neustadt, P.C.

[57] ABSTRACT

Process for the preparation of amides via the catalytic rearrangement of oximes which comprises putting an oxime in vapor phase in contact with a catalyst selected from a mesoporous silica-alumina having a molar ratio $SiO/Al_2O_2$ of between 20 and 1000, an average pore diameter of between 20 and 100 Å and an X-ray diffraction pattern (XRD) from powders which, after calcination, has the deepest reflection at d-spacing of more than 18 Å ($2\theta<4.9°$, CuKα radiation).

6 Claims, No Drawings

PROCESS FOR THE PREPARATION OF AMIDES FROM OXIMES

The present invention relates to a process for the preparation of amides from oximes.

More specifically, the present invention relates to the use of silica-aluminas with a high surface area and high pore volume in the catalytic transformation of oximes, such as cyclohexanone oxime, to amides, such as ε-caprolactam (caprolactam), also known as Beckmann catalytic rearrangement.

Amides, and in particular caprolactam, are known in literature as important intermediates for chemical syntheses and as raw materials for the preparation of polyamide resins.

Caprolactam is at present produced industrially by cyclohexanone oxime rearrangement in liquid phase using sulfuric acid or oleum. The rearranged product is neutralized with ammonia causing the joint formation of ammonium sulfate. This technology has numerous problems linked to the use of sulfuric acid, to the formation of high quantities of ammonium sulfate, with relative problems of disposal, corrosion of the equipment owing to the presence of acid vapours, etc.

Alternative processes have been proposed in literature for the catalytic rearrangement of cyclohexanone oxime into caprolactam, in which solids of an acid nature are used, as catalysts, selected from derivatives of boric acid, zeolites, non-zeolitic molecular sieves, solid phosphoric acid, mixed metal oxides, etc.

In particular, European patent 234.088 describes a method for preparing caprolactam which comprises putting cyclohexanone oxime in gaseous state in contact with alumino-silicates of the zeolitic type such as ZSM-5, ZSM-11 or ZSM-23 having a "Constraint Index" of between 1 and 12, an atomic ratio Si/Al of at least 500 ($SiO_2/Al_2O_3$ of at least 1,000) and an external acid functionality of less than 5 micro equivalents/g.

Zeolites, as described in "Zeolite Molecular Sieves" D. W. Breck, John Wiley & Sons, (1974) or in "Nature" 381 (1996), 295, are crystalline products characterized by the presence of a regular microporosity, with channels having dimensions of between 3 and 10 Å. In some particular zeolitic structures there can be cavities with greater dimensions, of up to about 13 Å.

In addition, zeolites can be identified by typical X-ray diffraction patterns of three-dimensional lattices, with Bragg reflections present within a wide spectral range. The more significant ones are generally within the 2θ angular range of between 3 and 60°, CuKα radiation.

With the aim of providing another method for the preparation of amides, and in particular of caprolactam, the Applicant has now found a new process which uses an acid catalyst, selected from silica-aluminas, having particular morphological and structural properties as described below, characterized by a considerable catalytic activity, a high selectivity, practically regardless of the conversion, and the possibility of being regenerated by thermal treatment.

The present invention therefore relates to a process for the preparation of amides via the catalytic rearrangement of oximes which comprises putting an oxime in vapour phase in contact with a catalyst selected from a mesoporous silica-alumina having a molar ratio $SiO_2/Al_2O_2$ of between 20 and 1000, an average pore diameter of between 18 and 100 Å and an X-ray diffraction pattern (XRD) from powders which, after calcination, has the deepest reflection at d-spacing of more than 18 Å (2θ<4.9°, CuKα radiation). In addition, further reflections at a d-spacing of more than 10 Å (2θ<8.8°, radiation CuKα) can also be present. These materials therefore have Bragg reflections within a much narrower spectral range than zeolitic materials.

Examples of preferred catalysts according to the present invention are silica-aluminas, having a molar ratio $SiO_2/Al_2O_2$ of between 25 and 500, a specific surface area of between 500 and 1,500 $m^2/g$ and an average pore diameter of between 20 and 60 Å. These materials are known in literature and described, together with the methods for their preparation, in published International patent application WO/11.390, in Nature, 368 (1994), 321 or in Chemical Communication, (1996), 981.

More specifically, the silica-aluminas used in the process of the present invention can be obtained starting from a mixture containing at least one silica source, an alumina source, an organic compound having the formula:

$$R_1R_2R_3R_4\text{—OH} \qquad (I)$$

wherein at least one of $R_1$, $R_2$, $R_3$ and $R_4$ represents an aryl or alkyl group with a long chain ($C_6$–$C_{36}$) and each of the remaining $R_1$, $R_2$, $R_3$ and $R_4$ is selected from hydrogen and an alkyl group with a short chain ($C_1$–$C_5$). A second quaternary ammonium base having the above formula can also be present, in which, however, $R_1$, $R_2$, $R_3$ and $R_4$ are selected from hydrogen and an alkyl group with a short $C_1$–$C_5$ chain, or two of the alkyl groups can be jointly considered as forming a cyclic compound.

Alternatively, the organic compound (I) can be substituted with a linear amine such as dodecylamine.

The mixture is subjected to hydrothermal treatment at a temperature of between 25° and 250° C. for a time of between 5 minutes and 14 days. The catalyst thus obtained is active in the catalytic rearrangement of oximes when it is used in its acid form. Consequently, when necessary, there is a cationic exchange phase with the usual techniques.

According to the present invention the preferred amide is ε-caprolactam (caprolactam) and the preferred oxime is cyclohexanone oxime (CEOX). In particular, the catalytic rearrangement of the cyclohexanone oxime takes place at a pressure of between 0.05 and 10 bars and at a temperature of between 250° and 500° C., preferably between 300° and 450° C. More specifically, the cyclohexanone oxime, in vapour phase, is fed to the reactor containing the catalyst in the presence of a solvent and optionally an uncondensable gas. The cyclohexanone oxime is dissolved in the solvent and the mixture thus obtained is then vaporized and fed to the reactor.

Preferred solvents are of the type $R_1$—O—$R_2$ wherein $R_1$ is a $C_1$–$C_4$ alkyl chain and $R_2$ can be a hydrogen atom or an alkyl chain containing a number of carbon atoms less than or equal to $R_1$. These solvents can be used alone or mixed with each other or combined with an aromatic hydrocarbon such as benzene or toluene. Alcohols with a $C_1$–$C_2$ alkyl chain are particularly preferred.

The cyclohexanone oxime is fed to the rearrangement reactor with a weight ratio with respect to the catalyst which is such as to give a WHSV (Weight Hourly Space Velocity), expressed as Kg of cyclohexanone oxime/kg of catalyst/time, of between 0.1 and 50 $h^{-1}$, preferably between 0.5 and 20 $h^{-1}$.

The deterioration of the catalyst is due to the formation of organic residues which obstruct the pores of the catalyst and poison its active sites. The deterioration process is slow and depends on the operating conditions and in particular the space velocity, solvent, temperature, composition of the feeding. The catalytic activity however can be efficiently reintegrated by the combustion of the residues, by treatment in a stream of air and nitrogen at a temperature of between 450° and 600° C.

The following illustrative but non-limiting examples are provided for a better understanding of the present invention and for its embodiment.

EXAMPLE 1

Synthesis of catalyst A 0.3 g of aluminium isopropylate were dissolved in 70 g of an aqueous solution of cetyltrimethylammonium hydroxide, obtained by putting a solution at 20% by weight of cetyltrimethylammonium bromide in contact with an ion exchange resin in basic form. 55 g of tetraethylorthosilicate diluted in 100 g of ethyl alcohol were added to this solution, operating at room temperature.

The precipitate obtained was left to rest at room temperature for 2 hours, then filtered, washed by redispersion in water and again filtered. The solid was then dried at 100° C. for 2 hours and then calcined at 550° C. for 5 hours in air.

The product obtained, analyzed by X-ray diffraction analysis from powders, registered by means of a Philips vertical diffractometer, equipped with a proportional impulse counter, divergent and recipient slides of 1/6° and with CuKα radiation ($\lambda$=1.54178 Å), has the deepest reflection at about 38 Å.

Upon chemical analysis, the sample has a molar ratio $SiO_2/Al_2O_3$ =330.

The specific surface area, measured with the B.E.T. method by adsorption-desorption cycles of $N_2$, at the temperature of liquid nitrogen (77 K), using a Carlo Erba Sorptomatic 1900 instrument, is 986 $m^2/g$.

The average pore diameter, determined by Dollimore/Heal elaboration, which is also applied to the adsorption/desorption curves of $N_2$ at the temperature of liquid nitrogen, is 26 Å.

EXAMPLE 2

Synthesis of the catalyst B

The same procedure is used as in example 1 but in the presence of 0.5 g of aluminum isopropylate.

The product obtained has the deepest reflection with X-rays at about 38 Å.

The specific surface area is equal to 1,100 $m^2/g$, with an average pore diameter centred at about 24 Å.

Upon chemical analysis the sample has a molar ratio $SiO_2/Al_2O_3$ =190.

EXAMPLES 3–7

Synthesis of catalysts C–G

To a first solution containing 52 g of ethanol, 8.3 g of dodecylamine and 13.5 g of water, a second solution is added, obtained by mixing 26 g of ethanol, 34.7 g of tetraethylorthosilicate and a varying quantity of aluminum sec-butoxide in order to obtain reagent mixtures with molar ratios $SiO_2/Al_2O_3$ equal to 50, 100, 300 500 (catalysts C–F). For the preparation of catalyst G, the addition of the aluminum compound is omitted.

The precipitates obtained are left to rest at room temperature for 2 hours, then filtered, washed by redispersion in water and again filtered. The solids are then dried at 100° C. for 2 hours, then calcined at 550° C. for 5 hours in air.

All the products obtained show with X-rays a deep peak at d-spacing of between 35 and 40 Å.

The specific surface area is respectively equal to 1,000, 1,100, 955, 987, 795 $m^2/g$, with an average pore diameter centred respectively at about 20, 26, 36, 36, 40 Å. Upon chemical analysis they have a molar ratio $SiO_2/Al_2O_3$=26, 75, 209, 442 respectively. In catalyst G the molar content of $Al_2O_3$ is less than 50 ppm.

EXAMPLES 8–14

The catalysts, granulated to 42–80 mesh, are charged into a glass reactor (length 20 cm, internal diameter 1 cm) preheated to 380° C. in nitrogen and dried for 1 hour. A mixture of $MeOH/N_2$ at a molar ratio 5/1 is then sent on the catalyst for 30 minutes.

After this pretreatment, the catalytic test is started by feeding a mixture of $CEOX/MeOH/N_2$ preheated and vaporized (WHSV=2.2$h^{-1}$, molar ratio 1/40/8). The temperature of the catalytic bed is maintained at 380° C.

The mixture of the effluent products from the reactor is condensed and analyzed via gaschromatography The conversion data of the cyclohexanone oxime and seletivity to caprolactam (CPL) are indicated in Table I.

TABLE I

| Example | Catalyst | t(h) | % Conv. | % Select. |
|---------|----------|------|---------|-----------|
| 8 | A | 1 | 97.8 | 76.8 |
|   |   | 20 | 84.1 | 78.8 |
| 9 | B | 1 | 100.0 | 72.8 |
|   |   | 24 | 94.5 | 77.0 |
| 10 | C | 3 | 99.8 | 62.3 |
|   |   | 24 | 99.8 | 73.7 |
| 11 | D | 1 | 99.9 | 69.7 |
|   |   | 24 | 100.0 | 78.1 |
| 12 | E | 1 | 100.0 | 68.8 |
|   |   | 24 | 100.0 | 75.7 |
| 13 | F | 1 | 99.9 | 66.5 |
|   |   | 24 | 99.4 | 70.9 |
| 14 | G | 1 | 10.7 | 64.1 |
|   |   | 24 | 6.9 | 37.7 |

EXAMPLE 15

The stability over a period of time of the performances of catalyst E was evaluated operating as above. The data are indicated in Table II.

TABLE II

| t(h) | % Conv. | % Select. |
|------|---------|-----------|
| 1 | 100.0 | 68.8 |
| 2 | 100.0 | 72.8 |
| 10 | 100.0 | 77.3 |
| 19 | 100.0 | 76.1 |
| 21 | 100.0 | 76.3 |
| 23 | 100.0 | 75.7 |
| 25 | 100.0 | 77.2 |
| 34 | 99.9 | 74.3 |
| 44 | 99.7 | 75.2 |

We claim:

1. A process for the preparation of ε-caprolactam via the catalytic rearrangement of oximes which comprises contacting cyclohexanone oxime in vapor phase with a catalyst selected from a mesoporous silica-alumina having a molar ratio $SiO_2/Al_2O_3$ of between 20 and 442, an average pore diameter of between 20 and 100 Å, an X-ray diffraction pattern (XRD) from powders which, after calcination, has the deepest reflection at d-spacing of more than 18 Å (2θ<4.9°, CuKα radiation), and a specific surface area of between 500 and 1,500 $m^2/g$.

2. The process according to claim 1, wherein the catalyst has an average pore diameter of between 20 and 60 Å.

3. The process according to claim 1, wherein the catalytic rearrangement of the oxime takes place at a pressure of between 0.05 and 10 bars and at a temperature of between 250° and 500° C.

4. The process according to claim 3, or wherein the catalytic rearrangement of the oxime takes place in the presence of a solvent.

5. The process according to claim 4, wherein the solvent is selected from products having the formula $R^1$—O—$R^2$ wherein $R^1$ is a $C_1$–$C_4$ alkyl chain and $R^2$ a hydrogen atom or an alkyl chain containing a number of carbon atoms less than or equal to $R^1$.

6. The process according to any of the claims from 3 to 5, wherein the oxime is fed to the rearrangement reactor with a weight ratio with respect to the catalyst which is such as to give a WHSV (Weight Hourly Space Velocity), expressed as Kg of oxime/kg of catalyst/time, from 0.1 to 50 $h^{-1}$.

* * * * *